(12) United States Patent
Georgeson et al.

(10) Patent No.: US 10,054,567 B2
(45) Date of Patent: Aug. 21, 2018

(54) MULTI-LAYER ULTRASOUND IMAGERS

(71) Applicant: The Boeing Company, Chicago, IL (US)

(72) Inventors: Gary E. Georgeson, Tacoma, WA (US); Tyler Holmes, Seattle, WA (US); Jeffrey R. Kollgaard, Seattle, WA (US)

(73) Assignee: The Boeing Company, Chicago, IL (US)

( * ) Notice: Subject to any disclaimer, the term of this patent is extended or adjusted under 35 U.S.C. 154(b) by 371 days.

(21) Appl. No.: 15/005,137

(22) Filed: Jan. 25, 2016

(65) Prior Publication Data

US 2017/0212083 A1 Jul. 27, 2017

(51) Int. Cl.
*G01N 29/06* (2006.01)
*G01N 29/04* (2006.01)
(Continued)

(52) U.S. Cl.
CPC ......... *G01N 29/069* (2013.01); *G01N 29/043* (2013.01); *G01N 29/07* (2013.01);
(Continued)

(58) Field of Classification Search
CPC .... G01N 29/069; G01N 29/043; G01N 29/07; G01N 29/221; G01N 29/2437; G01N 29/262; G01N 29/38; G01N 2291/103; G01N 2291/106; G10K 11/18; G10K 11/345; A61B 2017/0011; A61B 2017/00402; B06B 1/0618; B06B 3/00;
(Continued)

(56) References Cited

U.S. PATENT DOCUMENTS 4,880,010 A * 11/1989 Szilard ................. B06B 1/0622
600/457
7,478,569 B2    1/2009 Bossi et al.
(Continued)

OTHER PUBLICATIONS

Phased Array Ultrasounds, https://en.wikipedia.org/wiki/Phased_array_ultrasonics, Jan. 8, 2016.
(Continued)

*Primary Examiner* — Manish S Shah
*Assistant Examiner* — Rose M Miller
(74) *Attorney, Agent, or Firm* — Duft Bornsen & Fettig LLP

(57) ABSTRACT

Systems and methods for multi-layer ultrasonic imaging are provided. One embodiment is an apparatus that includes linear ultrasonic transducers that are each configured to conduct electricity across their length. The apparatus includes a first planar layer that comprises a first set of the transducers arranged in parallel. The apparatus also includes a second planar layer that comprises a second set of the transducers arranged in parallel, and that is oriented such that each transducer of the second set overlaps at least two transducers of the first set. Furthermore, the apparatus includes a third planar layer that comprises a third set of the transducers arranged in parallel, and that is oriented such that each transducer of the third set overlaps at least two transducers of the first set and at least two transducers of the second set.

22 Claims, 9 Drawing Sheets

(51) Int. Cl.
*G01N 29/07* (2006.01)
*G01N 29/22* (2006.01)
*G01N 29/24* (2006.01)
*G01N 29/26* (2006.01)
*G01N 29/38* (2006.01)

(52) U.S. Cl.
CPC ....... *G01N 29/221* (2013.01); *G01N 29/2437* (2013.01); *G01N 29/262* (2013.01); *G01N 29/38* (2013.01); *G01N 2291/103* (2013.01)

(58) Field of Classification Search
CPC ....... B06B 3/12; B06B 7/026; H01L 41/0831; H01L 41/0913; H01L 41/083
USPC .......... 73/598, 632, 641, 642; 310/322, 334, 310/336, 367, 368
See application file for complete search history.

(56) References Cited

U.S. PATENT DOCUMENTS

| | | |
|---|---|---|
| 7,712,369 B2 | 5/2010 | Georgeson |
| 8,332,165 B1 | 12/2012 | Tat et al. |
| 8,453,928 B2 | 6/2013 | Baarstad et al. |
| 8,662,395 B2 | 3/2014 | Melandso et al. |
| 8,965,100 B2 | 2/2015 | Lin et al. |
| 2008/0309200 A1* | 12/2008 | Melandso ............... B06B 1/064 310/334 |
| 2009/0156940 A1* | 6/2009 | Yen ....................... B06B 1/0633 600/459 |
| 2014/0333758 A1 | 11/2014 | Wu et al. |
| 2015/0053013 A1* | 2/2015 | Baarstad ................ G01N 29/26 73/620 |

OTHER PUBLICATIONS

U.S. Appl. No. 13/928,870, filed Jun. 27, 2013, Robert B. Greegor, Richard H. Bossi, John Z. Lin, Hong H. Tat, Alan F. Stewart.
U.S. Appl. No. 14/049,974, filed Oct. 9, 2013, Gary E. Georgeson Tacoma, WA (US), William Joseph Tapia Graham, WA (US), Michael D. Fogarty Auburn, WA (US), Hong Hue Tat Redmond, WA (US), Richard H. Bossi Renton, WA (US), Robert L. Carlsen.
U.S. Appl. No. 14/797,462, filed Jul. 13, 2015, Tyler M. Holmes Seattle, WA (US), Jeffrey R. Kollgaard Seattle, WA (US), Gary E. Georgeson Tacoma, WA (US).
U.S. Appl. No. 14/809,522, filed Jul. 27, 2015, Tyler M. Holmes Seattle, WA (US), Jeffrey R. Kollgaard Seattle, WA (US), Gary E. Georgeson Tacoma, WA (US).

* cited by examiner

MULTI-LAYER ULTRASOUND IMAGERS

FIELD

The disclosure relates to the field of imaging, and in particular, to ultrasonic imaging.

BACKGROUND

Ultrasonic imaging is utilized in a variety of fields in order to detect hidden sub-surface features in objects. For example, ultrasonic imaging may be used to identify the internal structure of a multi-layer composite part. This provides a substantial benefit by enabling the detection of hidden wrinkles, delaminations, or other inconsistencies within the composite part. In composite parts that are subject to substantial loads, or that are mission critical (e.g., a wing of an aircraft), inspection processes are particularly important because they allow for inconsistencies to be detected.

While ultrasonic imaging is a feasible technique for detecting the presence of wrinkles and other inconsistencies within a composite part, current ultrasonic imaging equipment remains complex and expensive. Thus, users continue to desire ultrasonic imaging systems that are highly effective, yet also affordable.

SUMMARY

Embodiments described herein include ultrasonic imagers that are capable of pinpointing the position of an ultrasonic wave that has been reflected off of an object being imaged. These ultrasonic imaging devices utilize multiple layers of transducers. The transducers in each layer are parallel with respect to each other, and each layer is rotated with respect to the other layers about an axis. This means that the transducers in one layer cross over transducers in other layers. Thus, the location of a returning ultrasonic wave may be determined based on the location at which detecting transducers in different layers intersect.

One embodiment is an apparatus that includes ultrasonic transducers that are each configured to conduct electricity across their length. The apparatus includes a first planar layer that comprises a first set of the transducers arranged in parallel. The apparatus also includes a second planar layer that comprises a second set of the transducers arranged in parallel, and that is oriented such that each transducer of the second set overlaps at least two transducers of the first set. Furthermore, the apparatus includes a third planar layer that comprises a third set of the transducers arranged in parallel, and that is oriented such that each transducer of the third set overlaps at least two transducers of the first set and at least two transducers of the second set.

A further embodiment is an apparatus that includes ultrasonic transducers which are arranged into layers that are each rotated a different angle about an axis that is perpendicular to the layers. The apparatus also includes a controller that is configured to selectively control the transducers in each of the layers to transmit and receive ultrasonic waves. For example, the controller may transmit an ultrasonic wave via an ultrasonic transducer of a first of the layers, detect a returning ultrasonic wave at a receiving ultrasonic transducer of a second of the layers, detect the returning ultrasonic wave at a receiving ultrasonic transducer of a third of the layers, and identify a position corresponding to an intersection of the receiving ultrasonic transducers.

Another embodiment is a method for ultrasonic imaging. The method includes transmitting an ultrasonic wave via a transmitting ultrasonic transducer located within a first layer of an ultrasonic imaging apparatus that is rotated a first angle about an axis that is perpendicular to the first layer. The method also includes detecting a returning ultrasonic wave at a receiving ultrasonic transducer located within a second layer of an ultrasonic imaging apparatus that is rotated a second angle about the axis, and detecting the returning ultrasonic wave at a receiving ultrasonic transducer located within a third layer of an ultrasonic imaging apparatus that is rotated a third angle about the axis. Further, the method includes identifying a surface location corresponding to an intersection of the receiving ultrasonic transducers.

Another embodiment is a non-transitory computer readable medium embodying programmed instructions which, when executed by a processor, are operable for performing a method. The method includes transmitting an ultrasonic wave via a transmitting ultrasonic transducer located within a first layer of an ultrasonic imaging apparatus that is rotated a first angle about an axis that is perpendicular to the first layer. The method also includes detecting a returning ultrasonic wave at a receiving ultrasonic transducer located within a second layer of an ultrasonic imaging apparatus that is rotated a second angle about the axis, and detecting the returning ultrasonic wave at a receiving ultrasonic transducer located within a third layer of an ultrasonic imaging apparatus that is rotated a third angle about the axis. Further, the method includes identifying a surface location corresponding to an intersection of the receiving ultrasonic transducers.

Other exemplary embodiments (e.g., methods and computer-readable media relating to the foregoing embodiments) may be described below. The features, functions, and advantages that have been discussed can be achieved independently in various embodiments or may be combined in yet other embodiments further details of which can be seen with reference to the following description and drawings.

DESCRIPTION OF THE DRAWINGS

Some embodiments of the present disclosure are now described, by way of example only, and with reference to the accompanying drawings. The same reference number represents the same element or the same type of element on all drawings.

DESCRIPTION

The figures and the following description illustrate specific exemplary embodiments of the disclosure. It will thus be appreciated that those skilled in the art will be able to devise various arrangements that, although not explicitly described or shown herein, embody the principles of the disclosure and are included within the scope of the disclosure. Furthermore, any examples described herein are intended to aid in understanding the principles of the disclosure, and are to be construed as being without limitation to such specifically recited examples and conditions. As a result, the disclosure is not limited to the specific embodiments or examples described below, but by the claims and their equivalents.

Figure 1:
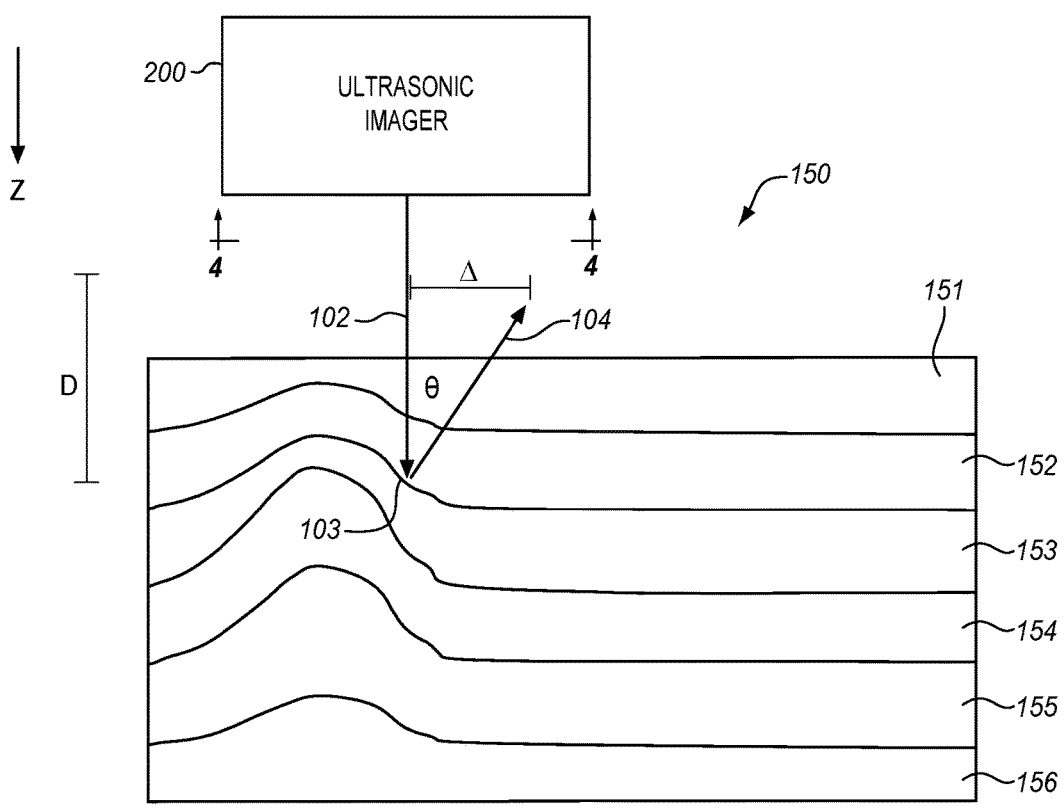
FIG. 1 is a diagram of ultrasonic imaging in an exemplary embodiment.

FIG. 1 is a diagram illustrating transmission and reflection of an ultrasonic wave in an exemplary embodiment. As shown in FIG. 1, a transmitted ultrasonic wave 102 is sent in a direction (Z) by an ultrasonic imager 200 into a multi-layer composite part 150 comprising layers 151-156. When the transmitted ultrasonic wave strikes a boundary 103 between layers 152 and 153 of part 150, a returning ultrasonic wave 140 is generated. Depending on the orientation of the boundary between the layers, returning ultrasonic wave 104 may be displaced upon arrival at imager 200 by some distance ($\Delta$). This distance of displacement, when analyzed in combination with the depth (D) of the location being imaged, may be used to extract a value ($\theta$) indicating an angle of a wrinkle at the location being imaged. In general, the larger the value of ($\Delta$), the larger the value of ($\theta$). A higher value of ($\theta$) indicates the presence of an inconsistency that is more intense (e.g., "kinked" at a greater angle with respect to its surroundings) within the layers of part 150.

Receivers/transducers that are being used to image the returning ultrasonic wave 104 may be gated to acquire input only during a range of times after the transmitted ultrasonic wave has been sent, and may also be gated to only acquire input at a range of amplitudes (e.g., in order to filter out noise). The range of times chosen as gate values determines the depth that is being imaged within part 150. Specifically, a range of times corresponding to a longer period of time results in a deeper portion of object 150 being imaged by ultrasonic imager 200.

Figure 2:
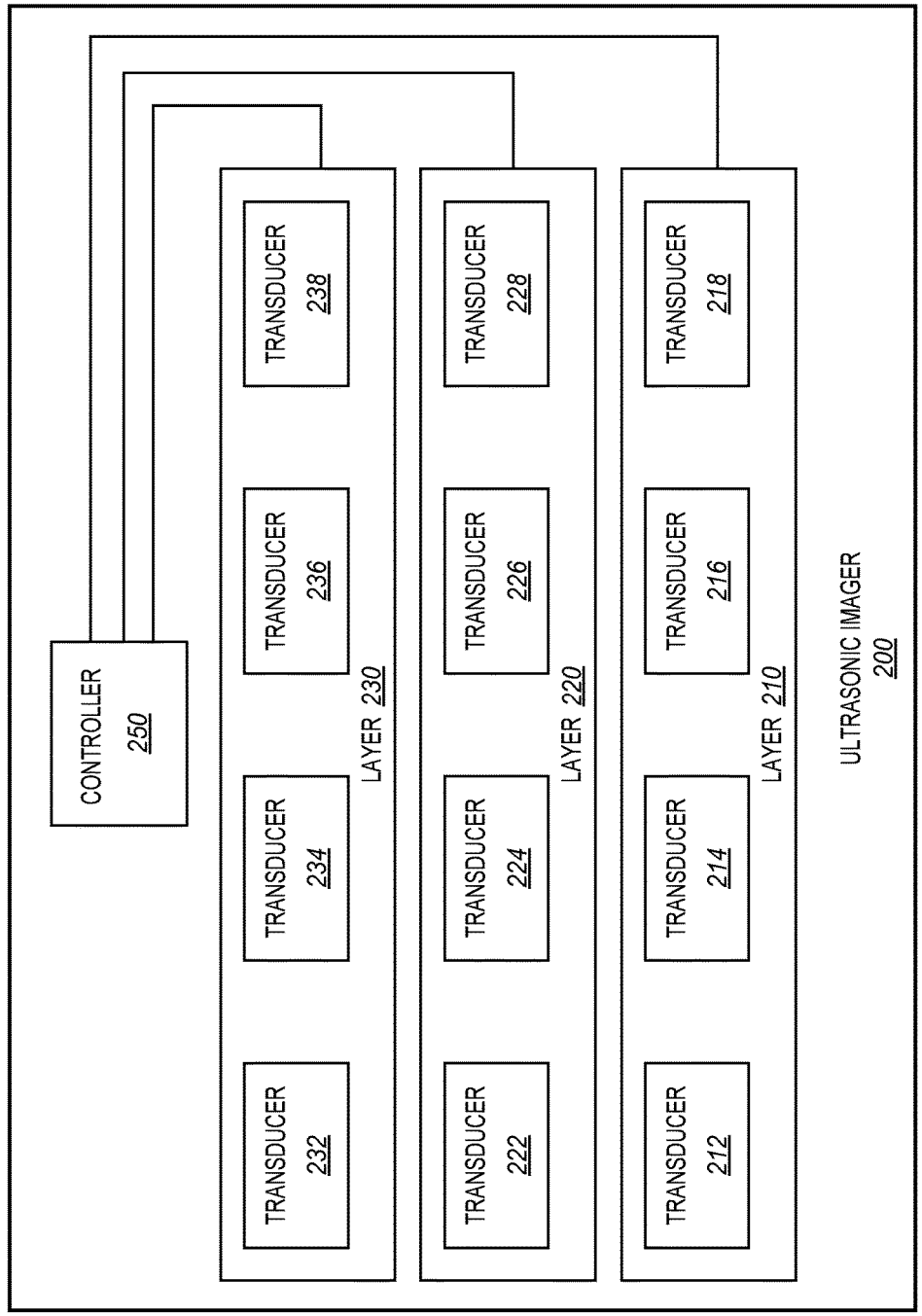
FIG. 2 is a block diagram of an ultrasonic imager in an exemplary embodiment.
Figure 3:
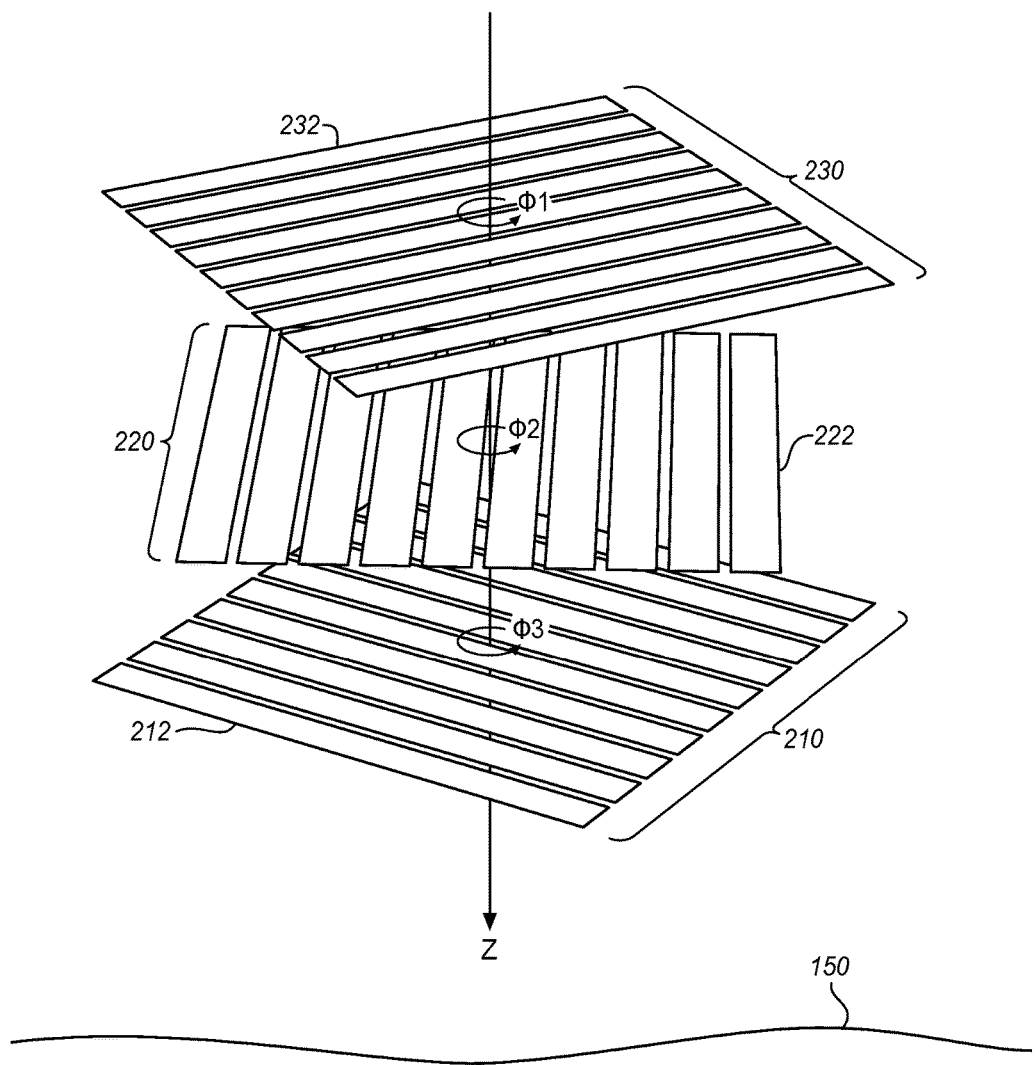
FIGS. 3-4 illustrate transducers grouped into layers for an ultrasonic imager in an exemplary embodiment.

FIG. 2 is a block diagram of ultrasonic imager 200 in an exemplary embodiment. Ultrasonic imager 200 includes multiple planar layers (210, 220, 230) of linear transducers (e.g., 212, 222, 232). Each layer includes transducers that are oriented parallel to each other. For example, layer 210 includes transducers 212, 214, 216, and 218, layer 220 includes transducers 222, 224, 226, and 228, and layer 230 includes transducers 232, 234, 236, and 238. The transducers (e.g., 212, 222, 232) in each layer are rotated with respect to transducers (e.g., 212, 222, 232) in other layers, as is illustrated in FIG. 3. The transducers (e.g., 212, 222, 232) described herein comprise any suitable components capable of transmitting and/or receiving ultrasonic waves. In one embodiment, the transducers (e.g., 212, 222, 232) comprise linear piezoelectric elements (e.g., piezoresistors) that vibrate in response to receiving an ultrasonic wave, resulting in a detectable change in current. Such piezoelectric elements may also be operated by driving current through them, causing the piezoelectric elements to vibrate and thereby transmit ultrasonic waves. Controller 250 is configured to direct the operations of the various transducers described herein (e.g., 212, 222, 232) as the transducers generate and/or receive ultrasonic waves. Controller 250 may further be operable to identify a surface location at ultrasonic imager 200 corresponding to the location of a detected ultrasonic wave. Controller 250 may be implemented, for example, as custom circuitry, as a processor executing programmed instructions, or some combination thereof.

FIG. 3 illustrates an arrangement of transducers (e.g., 212, 222, 232) grouped into layers for ultrasonic imager 200 in an exemplary embodiment. FIG. 3 illustrates that each layer (210, 220, 230) is separated from the other layers along a direction (Z). The distance between layers shown in FIG. 3 is exaggerated for purposes of clarity. In embodiments where a substantial amount of vertical distance separates the layers, controller 250 may adjust gating parameters separately for each of the layers to ensure that each layer images object 150 at the same depth. In a further embodiment, the layers (210, 220, 230) may be separated by an electrically insulating interlayer, in order to ensure that electric interference does not result in noise or false signal detection while ultrasonic imager 200 is being operated.

Figure 4:
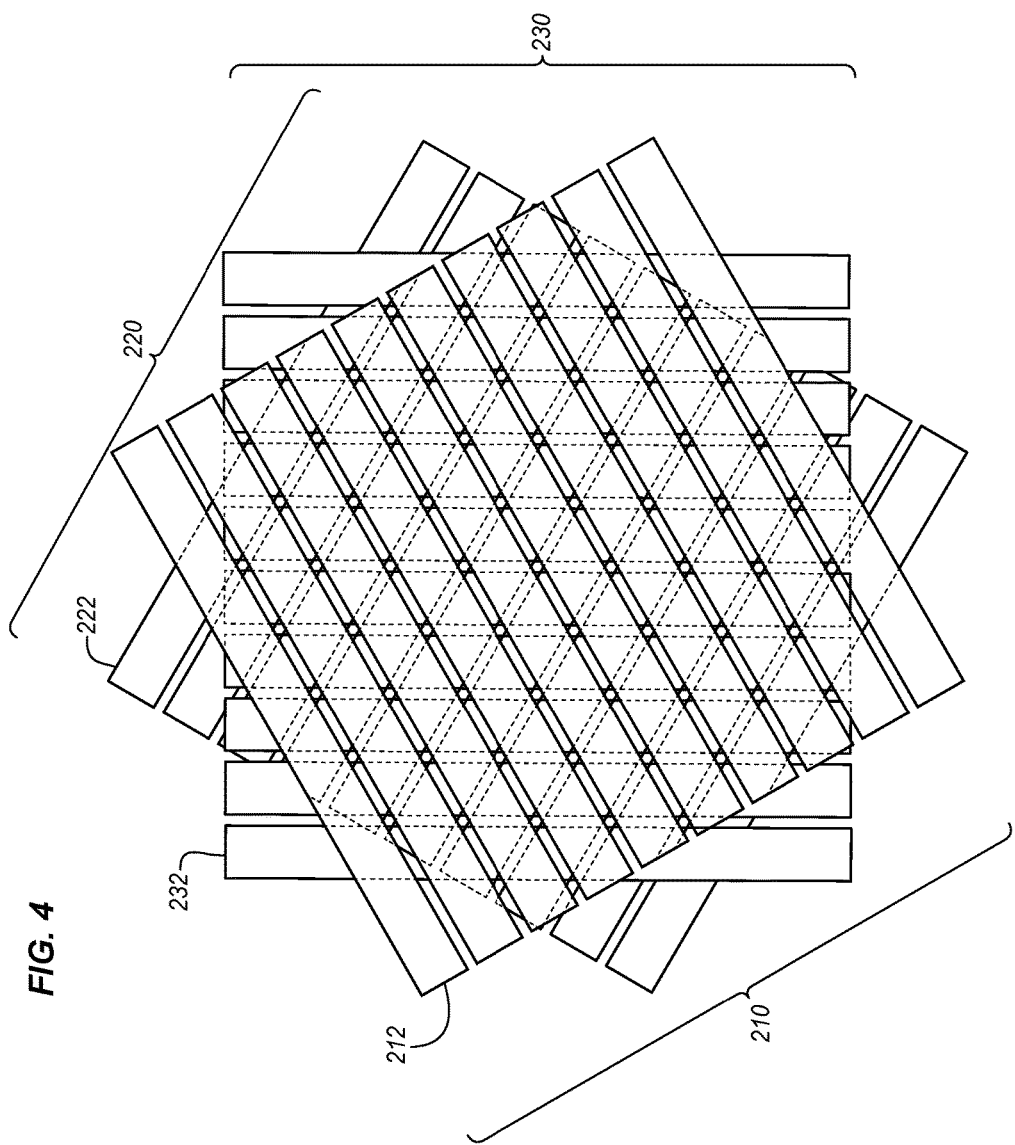

As shown in FIG. 3, each layer is rotated about the axis of direction Z by a different value (e.g., $\Phi 1$, $\Phi 2$, $\Phi 3$). Hence a transducer (212) in layer 210 will overlap at least one transducer (222) in layer 220, and at least one transducer (232) in layer 230. This cross-over between different transducers (e.g., 212, 222, 232) is particularly beneficial in implementations where the transducers (e.g., 212, 222, 232) are each implemented as a linear piezoelectric element. In these cases, even though individual transducers (e.g., 212, 222, 232) only provide resolution on a "line by line" basis, the intersection of two transducers (e.g., 222, 232) in different layers may be used to determine the exact location at which a returning ultrasonic wave was received at ultrasonic imager 200. The view shown in FIG. 4 is a head-on view of ultrasonic imager 200 indicated by view arrows 4. This view illustrates each of three layers utilized for ultrasonic imager 200, as they are "stacked" on top of each other.

Figure 5:
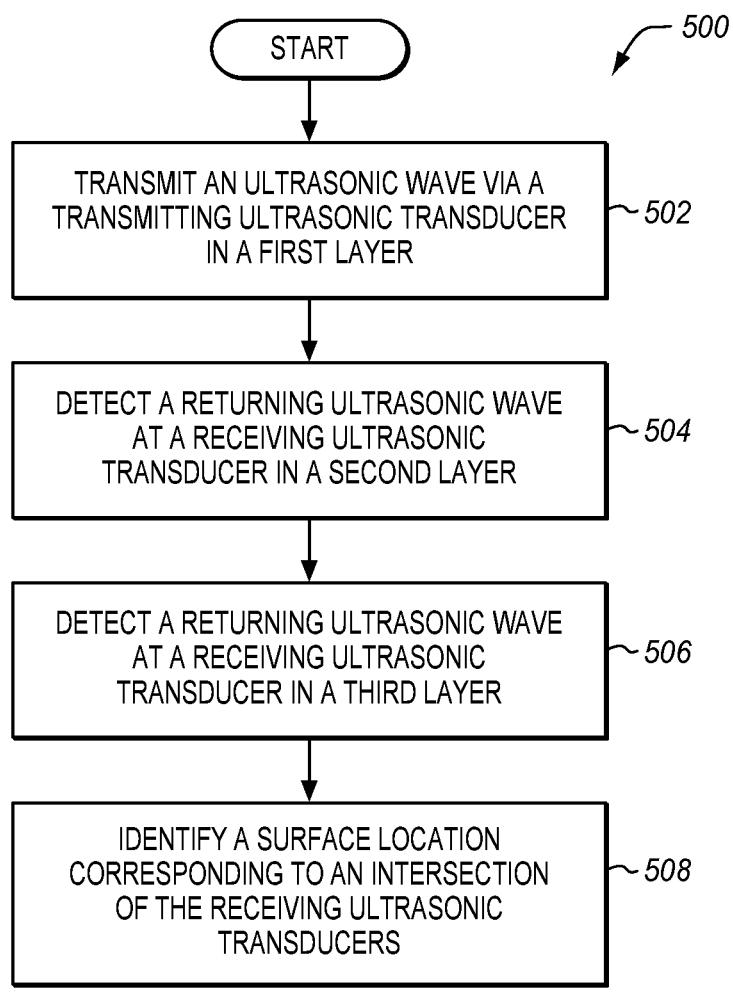
FIG. 5 is a flowchart illustrating a method for operating an ultrasonic imager in an exemplary embodiment.

Illustrative details of the operation of ultrasonic imager 200 will be discussed with regard to FIG. 5. Assume, for this embodiment, that object 150 (e.g., a composite part for an aircraft wing or fuselage) is being inspected for inconsistencies that are below the surface of object 150. FIG. 5 provides a technique for detecting not just the existence of inconsistencies within object 150, but also quantifying the size of those inconsistencies.

FIG. 5 is a flowchart illustrating a method 500 for utilizing an ultrasonic imager to detect inconsistencies in an object in an exemplary embodiment. The steps of method 500 are described with reference to ultrasonic imager 200 of FIG. 1, but those skilled in the art will appreciate that method 500 may be performed in other systems. The steps of the flowcharts described herein are not all inclusive and may include other steps not shown. The steps described herein may also be performed in an alternative order.

In step 502, controller 250 sends electrical current through a transducer 212 in a first layer 210 of ultrasonic imager 200, which causes transducer 212 to transmit an ultrasonic wave into object 150. Since controller 250 is driving current through transducer 212 to generate an ultrasonic wave, transducer 212 will not be used to detect a returning ultrasonic wave.

The transmitted ultrasonic wave continues through object 150 until it hits a location exhibiting a change in material properties, such a border between layers of constituent material within object 150. Upon hitting the location, a returning, reflected ultrasonic wave is generated. The returning ultrasonic wave returns back towards ultrasonic imager 200, but will be deflected in a direction if the location was not flat/normal with respect to the transmitted ultrasonic wave. The amount of deflection increases as the slope of the location deviates from an expected, normal configuration.

Thus, the degree of deviation exhibited by a kink or wrinkle in object 150 may be quantified by determining an amount of deflection applied to the returning ultrasonic wave.

To determine the location at which the returning ultrasonic wave was received, controller 250 engages in a gated listening process in steps 504-506. In step 504, controller 250 detects a returning ultrasonic wave at a transducer 222 of layer 220, while in step 506, controller 250 detects a returning ultrasonic wave at a transducer 232 of layer 230. In embodiments wherein ultrasonic imager 200 utilizes piezoelectric transducers, the returning ultrasonic wave will cause vibrations in the transducers (e.g., 212, 222, 232) that result in a detectable change in resistance at the transducer. In such an embodiment, the first transducer in a layer that detects the returning ultrasonic wave (e.g., 222) may be considered the detecting transducer for that layer.

In response to identifying the detecting transducer (e.g., 222, 232) at each of the other layers (e.g., layer 220 and layer 230), controller 250 identifies a surface location at imager 200 corresponding to an intersection of the receiving ultrasonic transducers (e.g., 222, 232) in step 508. This step may comprise consulting data stored in memory indicating locations on the surface of ultrasonic imager 200 occupied by each of the detecting transducers (e.g., 222, 232), and then calculating an intersection, or may comprise looking up a known surface location, based on the identity of the two detecting transducers (e.g., 222, 232). This surface location may then be output via a screen or display, transmitted for further analysis, or further analyzed by controller 250.

If the surface location corresponds with/lines up with the transducer 212 that originally generated the transmitted ultrasonic wave, then controller 250 may determine that no substantial inconsistency exists at the imaged depth underneath the transmitting transducer. In contrast, if the surface location does not align with the transmitting transducer, then the returning ultrasonic wave has been deflected by some angle θ and an inconsistency exists.

Figure 6:
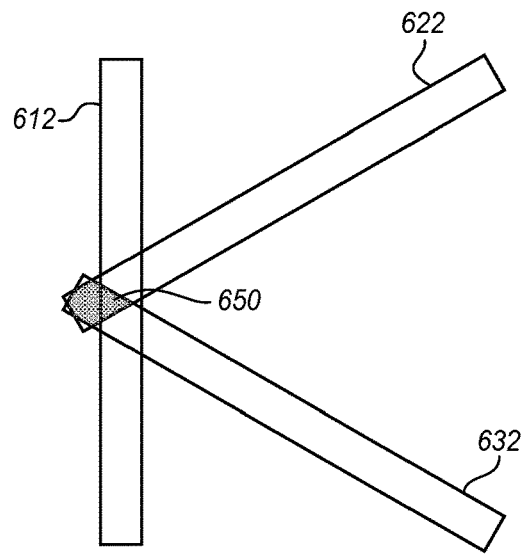
FIGS. 6-7 are diagrams illustrating scenarios in which no inconsistency is detected within an object being imaged.
Figure 7:
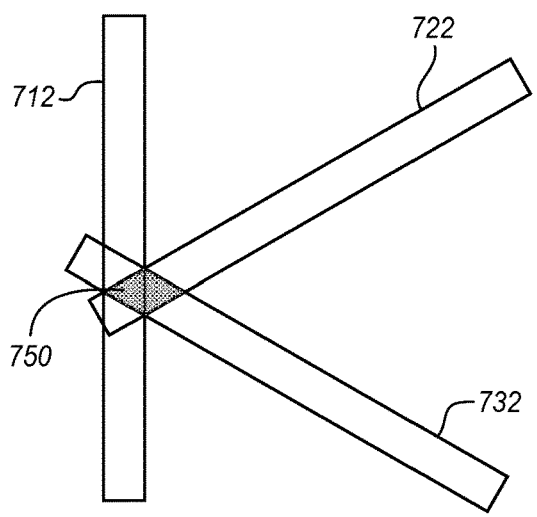

FIGS. 6-7 illustrate scenarios in which no inconsistency is detected within an object being imaged. In these scenarios, the returning ultrasonic wave has not been deflected away from the transmitting transducer (e.g., 212). For example, FIG. 6 illustrates a transmitting transducer 612, and two detecting transducers 622 and 632. In this example, the intersection 650 of transducers 622 and 612 is co-located with transmitting transducer 612. Hence, controller 250 may conclude that no substantial inconsistencies exist at the imaged depth and location. Similarly, FIG. 7 illustrates a transmitting transducer 712, and two detecting transducers 722 and 732. In this example, the intersection 750 of transducers 722 and 712 is co-located with transmitting transducer 712.

Figure 8:
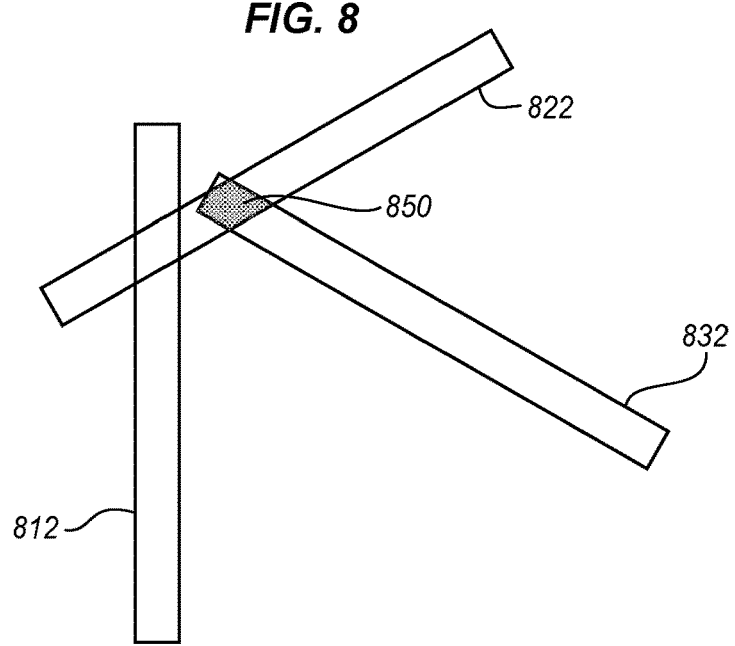
FIGS. 8-9 are diagrams illustrating scenarios in which an inconsistency is detected within an object being imaged.
Figure 9:
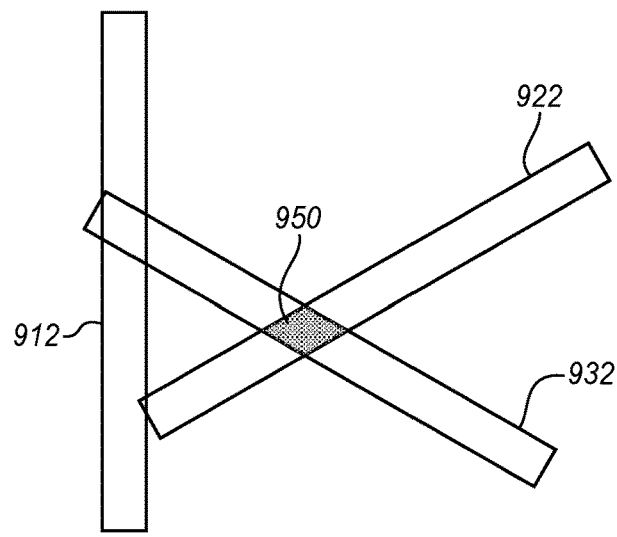

FIGS. 8-9 illustrate scenarios in which an inconsistency is detected within an object being imaged. In FIG. 8, transmitting transducer 812 is not co-located with intersection 850 of detecting transducers 822 and 832. Hence, the returning ultrasonic wave was deflected at an angle θ (e.g., as shown in FIG. 2). Similarly, in FIG. 9, transmitting transducer 912 is not co-located with intersection 950 of detecting transducers 922 and 932. Note that the intersection 950 is roughly parallelogram/diamond shaped in this embodiment, corresponding to the shape of overlapping portions of transducers 922 and 932.

In further embodiments, an ultrasonic imager may be used to identify wrinkles and other inconsistencies within object 150, and to quantify the nature of inconsistencies that exist underneath the surface of object 150. In one embodiment, controller 250 engages in further analysis to determine an angle of the detected inconsistency. This calculation may be performed via trigonometric functions based on the depth being imaged, and the distance between the identified surface location and the transmitting transducer (e.g., 212). For example, as shown in FIG. 1, controller 250 may determine that the tangent of θ is equal to depth (D) divided by the distance (Δ), and may calculate θ based on this relationship.

During operation, ultrasonic imager 200 may engage in multiple cycles of transmission and detection of ultrasonic waves. By transmitting ultrasonic waves from a different transducer in each cycle (e.g., a different transducer in the same layer, or a transducer in a different layer), controller 250 is capable of mapping inconsistencies along object 150. Controller 250 may also select a depth to be imaged, by gating the detection period used by the various transducers discussed herein.

Figure 10:
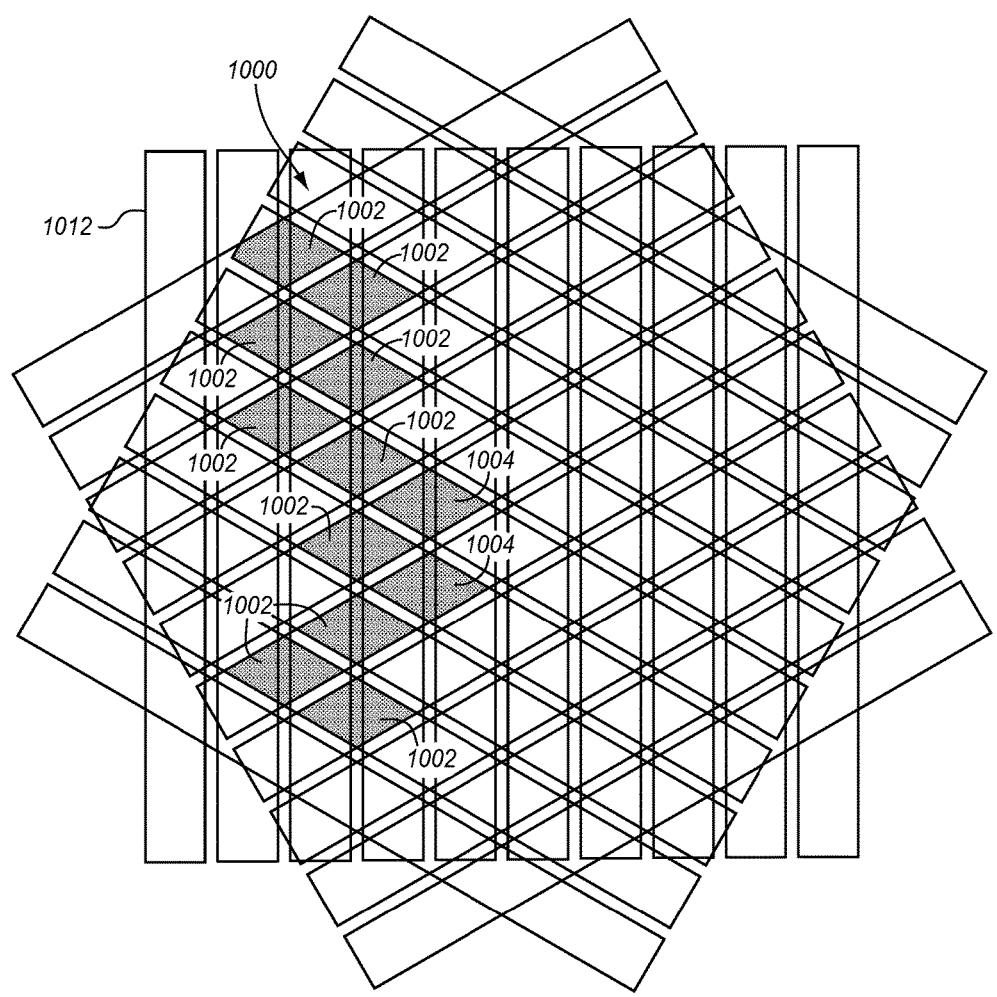
FIG. 10 is a diagram illustrating detected variations in a wrinkle in an object in an exemplary embodiment.

Controller 250 may further generate a map (e.g., a two dimensional (2D) or three dimensional (3D) map, depending on whether different depths are imaged) indicating the location and intensity of inconsistencies within object 150, based on these measurements. In this manner, off-angle reflections for individual strip "firings" are collected and combined over time by controller 250 to map the shape and intensity of inconsistencies within object 150. For example, FIG. 10 illustrates off-angle reflections caught during a time-of-flight period that are above a gated amplitude. In FIG. 10, parallelogram/diamond shaped locations 1002 correspond with the intersections of transducers that detect the returning ultrasonic wave at a first time, while locations 1004 correspond with the intersections of transducers that detect the returning ultrasonic wave at a second time fractionally later than the first time. Since locations 1002 and 1004 are not co-located with transmitting transducer 1012, they illustrate a wrinkle 1000 of varying intensity/angle along the length of transmitting transducer 1012

In yet a further embodiment, ultrasonic waves/beams are "steered" by controller 250 time-sequencing transmissions from adjacent transducers in the same layer (e.g., 212 and its neighbors) to collect reflection angles at various depths within object 150. In this embodiment, beam steering techniques (such as those used for phased array antennae) may be used to map wrinkle shape and intensity in composites and perform swept inspections of metals. In short controller 250 may fire multiple ultrasonic transducers from the first layer 210 in a timed sequence to generate a directional ultrasonic wave.

In yet another embodiment, controller 250 transmits ultrasonic waves/beams at one angle and expects receipt of a returning ultrasonic wave at an expected angle, distance and time. In this embodiment, variations in intensity and return location (from their expected values) may be used to identify and map wrinkles within object 150.

Although only three layers of transducers (210, 220, 230) are illustrated with respect to the discussion above that are each rotated 60° apart, any suitable number of layers, and/or angle between layers, may be utilized to engage in the ultrasonic imaging techniques described herein.

Figure 11:
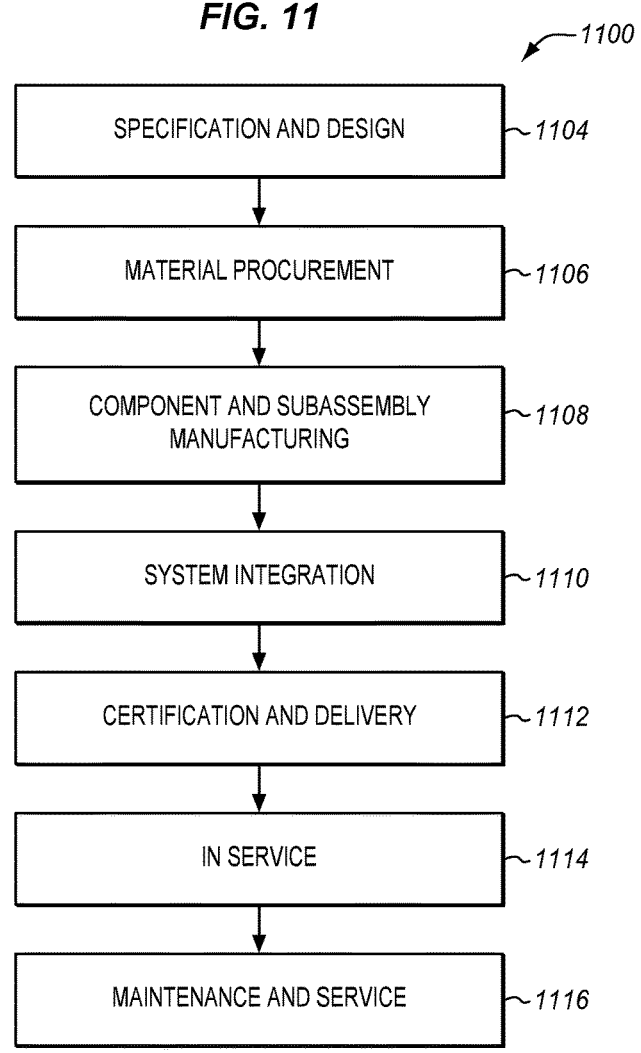
FIG. 11 is a flow diagram of aircraft production and service methodology in an exemplary embodiment.
Figure 12:
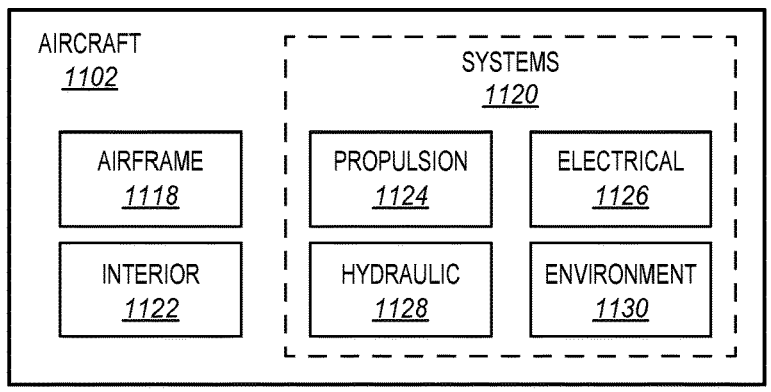
FIG. 12 is a block diagram of an aircraft in an exemplary embodiment.

Referring more particularly to the drawings, embodiments of the disclosure may be described in the context of an aircraft manufacturing and service method 1100 as shown in FIG. 11 and an aircraft 1102 as shown in FIG. 12. During pre-production, exemplary method 1100 may include specification and design 1104 of the aircraft 1102 and material procurement 1106. During production, component and subassembly manufacturing 1108 and system integration 1110 of the aircraft 1102 takes place. Thereafter, the aircraft 1102 may go through certification and delivery 1112 in order to be placed in service 1114. While in service by a customer, the aircraft 1102 is scheduled for routine maintenance and service 1116 (which may also include modification, reconfiguration, refurbishment, and so on). The inventive techniques and systems described herein may further be implemented, for example, as a part of material procurement 1106 (e.g., in order to quantify the quality of materials being procured), as a part of component and subassembly manufacturing (e.g., for purposes of quality control), in system integration 1110, during certification and delivery 1112 to facilitate quality control, in service 1114 to examine operating aircraft, and/or in maintenance and service 1116

Each of the processes of method 1100 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 12, the aircraft 1102 produced by exemplary method 1100 may include an airframe 1118 with a plurality of systems 1120 and an interior 1122. Examples of high-level systems 1120 include one or more of a propulsion system 1124, an electrical system 1126, a hydraulic system 1128, and an environmental system 1130. Any number of other systems may be included. Although an aerospace example is shown, the principles of the invention may be applied to other industries, such as the automotive industry.

Apparatus and methods embodied herein may be employed during any one or more of the stages of the production and service method 1100. For example, an ultrasonic imager may be utilized during component and subassembly manufacturing 1108 to verify part integrity, in system integration 1110, certification and delivery 1112, and/or during maintenance and service 1116. Also, one or more apparatus embodiments, method embodiments, or a combination thereof may be utilized during the production stages 1108 and 1110, for example, by substantially expediting assembly of or reducing the cost of inspecting an aircraft 1102. Similarly, one or more of apparatus embodiments, method embodiments, or a combination thereof may be utilized while the aircraft 1102 is in service, for example and without limitation, to maintenance and service 1116.

In one embodiment, ultrasonic imager 200 is utilized to inspect a portion of airframe 118 that was manufactured during component and subassembly manufacturing 1108. Ultrasonic imager 200 may be used to perform further inspections in system integration 1110, and in maintenance and service 1116, when object 150 may be discarded and replaced with a newly manufactured part 1116.

Any of the various computing elements shown in the figures or described herein may be implemented as hardware, software operating via a processor, firmware, or some combination of these. For example, an element may be implemented as dedicated hardware. Dedicated hardware elements may be referred to as "processors", "controllers", or some similar terminology. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, a network processor, application specific integrated circuit (ASIC) or other circuitry, field programmable gate array (FPGA), read only memory (ROM) for storing software, random access memory (RAM), non-volatile storage, logic, or some other physical hardware component or module.

Also, an element may be implemented as instructions executable by a processor or a computer to perform the functions of the element. Some examples of instructions are software, program code, and firmware. The instructions are operational when executed by the processor to direct the processor to perform the functions of the element. The instructions may be stored on storage devices that are readable by the processor. Some examples of the storage devices are digital or solid-state memories, magnetic storage media such as a magnetic disks and magnetic tapes, hard drives, or optically readable digital data storage media.

Although specific embodiments are described herein, the scope of the disclosure is not limited to those specific embodiments. The scope of the disclosure is defined by the following claims and any equivalents thereof.

The invention claimed is:

1. An apparatus comprising:
   linear ultrasonic transducers that are each configured to conduct electricity across their length;
   a first planar layer that comprises a first set of the transducers arranged in parallel;
   a second planar layer that comprises a second set of the transducers arranged in parallel, and that is oriented for each transducer of the second set to overlap at least two transducers of the first set;
   a third planar layer that comprises a third set of the transducers arranged in parallel, and that is oriented for each transducer of the third set to overlap at least two transducers of the first set and at least two transducers of the second set; and
   a controller that transmits an ultrasonic wave from a transmitting transducer in the first planar layer, detects a returning ultrasonic wave at a receiving transducer in the second planar layer, detects the returning ultrasonic wave at a receiving transducer in the third planar layer, and identifies a surface location corresponding to an intersection of the receiving ultrasonic transducers.

2. An apparatus comprising:
   linear ultrasonic transducers which are arranged into at least three layers that are each rotated a different angle with respect to each other about an axis that is perpendicular to the layers; and
   a controller that is configured to selectively control the transducers in each of the layers to transmit and receive ultrasonic waves by: transmitting an ultrasonic wave from a transmitting transducer in a first of the layers, detecting a returning ultrasonic wave at a receiving transducer in a second of the layers, detecting the returning ultrasonic wave at a receiving transducer in a third of the layers, and identifying a surface location corresponding to an intersection of the receiving ultrasonic transducers.

3. The apparatus of claim 2, wherein:
   the controller is configured to transmit an ultrasonic wave via an ultrasonic transducer of the first of the layers, to detect a returning ultrasonic wave at a receiving ultrasonic transducer of the second of the layers, detect the returning ultrasonic wave at a receiving ultrasonic transducer of the third of the layers; and identify a position corresponding to an intersection of the receiving ultrasonic transducers.

4. The apparatus of claim 3 wherein:
the controller is configured to select a depth being imaged by the ultrasonic wave, and to gate detection of the ultrasonic wave to a time period corresponding to the depth.

5. The apparatus of claim 3 wherein:
the controller is configured to fire multiple ultrasonic transducers from the first layer in a timed sequence to generate a directional ultrasonic wave.

6. The apparatus of claim 2 wherein:
the ultrasonic transducers comprise piezoelectric elements.

7. The apparatus of claim 2 wherein:
the apparatus comprises three layers, and
the first of the layers, second of the layers, and third of the layers are angled about the axis by thirty, sixty, and ninety degrees, respectively.

8. The apparatus of claim 2 wherein:
the controller is configured to detect subsurface features in an object being imaged by the ultrasonic wave, based on the identified position.

9. The apparatus of claim 2 wherein:
each of the layers is separated from other layers by an electrically insulating interlayer that is transparent to ultrasonic waves.

10. A method comprising:
transmitting an ultrasonic wave via a transmitting linear ultrasonic transducer located within a first layer of an ultrasonic imaging apparatus that is perpendicular to an axis;
detecting a returning ultrasonic wave at a receiving ultrasonic transducer located within a second layer of an ultrasonic imaging apparatus that is rotated a second angle about the axis with respect to the first layer;
detecting the returning ultrasonic wave at a receiving ultrasonic transducer located within a third layer of an ultrasonic imaging apparatus that is rotated a third angle about the axis with respect to the first layer, wherein the second angle and third angle differ; and
identifying a surface location corresponding to an intersection of the receiving ultrasonic transducers.

11. The method of claim 10 wherein:
transmitting the ultrasonic wave comprises driving electric current through a piezoelectric element of the ultrasonic transducer in the first layer.

12. The method of claim 10 further comprising:
detecting a subsurface feature in an object being imaged by the ultrasonic wave, based on the identified position.

13. The method of claim 10 further comprising:
recording a peak amplitude for the returning ultrasonic wave at each of the receiving transducers.

14. The method of claim 10 further comprising:
selecting a depth being imaged by the ultrasonic wave; and
gating detection of the ultrasonic wave to a time period corresponding to the depth.

15. The method of claim 10 further comprising:
firing multiple ultrasonic transducers from the first layer in a timed sequence to generate a directional ultrasonic wave.

16. The method of claim 10 further comprising:
detecting an angle of a subsurface feature of an object being imaged by the ultrasonic wave, by comparing the identified position to an expected position.

17. A non-transitory computer readable medium embodying programmed instructions which, when executed by a processor, are operable for performing a method comprising:
transmitting an ultrasonic wave via a transmitting linear ultrasonic transducer located within a first layer of an ultrasonic imaging apparatus that is perpendicular to an axis;
detecting a returning ultrasonic wave at a receiving ultrasonic transducer located within a second layer of an ultrasonic imaging apparatus that is rotated a second angle about the axis with respect to the first layer;
detecting the returning ultrasonic wave at a receiving ultrasonic transducer located within a third layer of an ultrasonic imaging apparatus that is rotated a third angle about the axis with respect to the first layer, wherein the second angle and third angle differ; and
identifying a surface location corresponding to an intersection of the receiving ultrasonic transducers.

18. The medium of claim 17 wherein:
transmitting the ultrasonic wave comprises driving electric current through a piezoelectric element of the ultrasonic transducer in the first layer.

19. The medium of claim 17 wherein the method further comprises:
detecting a subsurface feature in an object being imaged by the ultrasonic wave, based on the identified position.

20. The medium of claim 17 wherein the method further comprises:
recording a peak amplitude for the returning ultrasonic wave at each of the receiving transducers.

21. The medium of claim 17 wherein the method further comprises:
selecting a depth being imaged by the ultrasonic wave; and
gating detection of the ultrasonic wave to a time period corresponding to the depth.

22. The medium of claim 17 wherein the method further comprises:
firing multiple ultrasonic transducers from the first layer in a timed sequence to generate a directional ultrasonic wave.

* * * * *